United States Patent [19]

Shiber

[11] Patent Number: 5,007,896
[45] Date of Patent: * Apr. 16, 1991

[54] ROTARY-CATHETER FOR ATHERECTOMY

[75] Inventor: Samuel Shiber, Woburn, Mass.

[73] Assignee: Surgical Systems & Instruments, Inc., Mundelein, Ill.

[*] Notice: The portion of the term of this patent subsequent to Mar. 22, 2005 has been disclaimed.

[21] Appl. No.: 324,616

[22] Filed: Mar. 16, 1989

Related U.S. Application Data

[63] Continuation-in-part of Ser. No. 286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 78,042, Jul. 27, 1987, Pat. No. 4,819,634, Ser. No. 205,479, Jun. 13, 1988, Pat. No. 4,883,458, and Ser. No. 225,880, Jul. 29, 1988, Pat. No. 4,842,579, said Ser. No. 78,042, is a continuation-in-part of Ser. No. 18,083, Feb. 24, 1987, said Ser. No. 205,479, is a continuation-in-part of Ser. No. 18,083, , said Ser. No. 225,880, is a continuation-in-part of Ser. No. 18,083, , which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.$^5$ .............................................. A61B 17/32
[52] U.S. Cl. ..................................... 604/22; 606/159
[58] Field of Search ....................... 606/159, 170, 180; 604/22, 95, 264, 267

[56] References Cited

U.S. PATENT DOCUMENTS 4,819,634 4/1989 Shiber .............................. 604/95 X Primary Examiner—Robert A. Hafer
Assistant Examiner—Kerry Owens
Attorney, Agent, or Firm—Samuel Shiber

[57] ABSTRACT

An atherectomy system insertable into a human blood vessel over a flexible guide-wire for remotely cutting and removing an obstruction therein, having a diametrical stabilized torque transmitting flexible rotary-catheter equipped with a rotary coring means at its distal end and a motor connected to its proximal end.

22 Claims, 5 Drawing Sheets

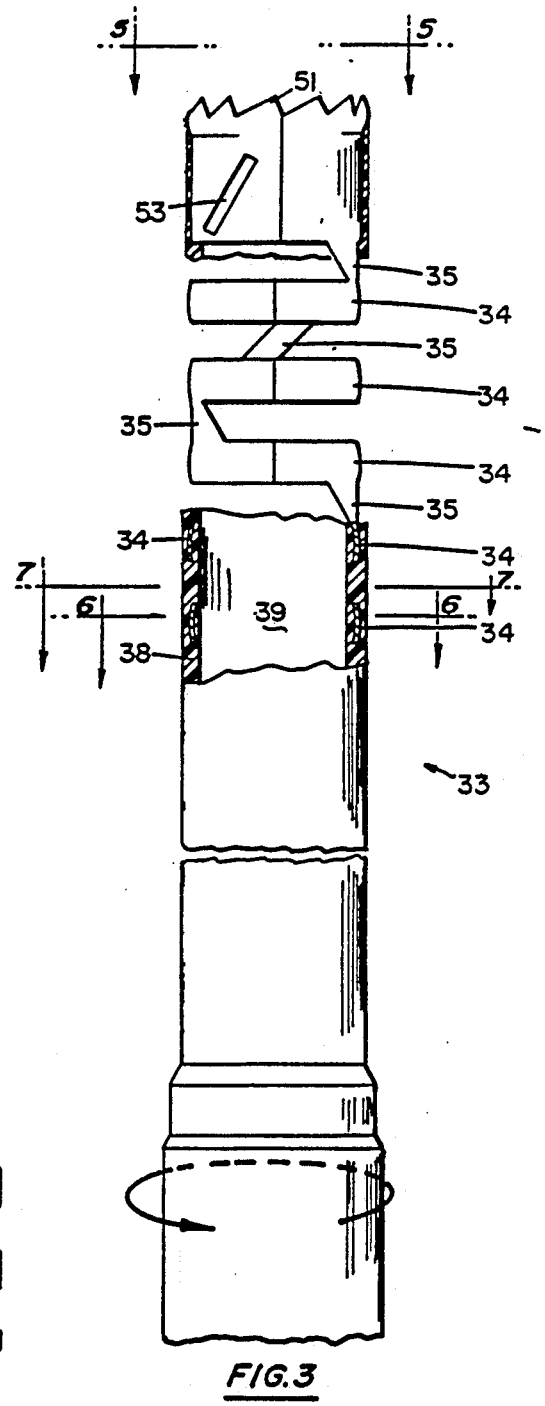
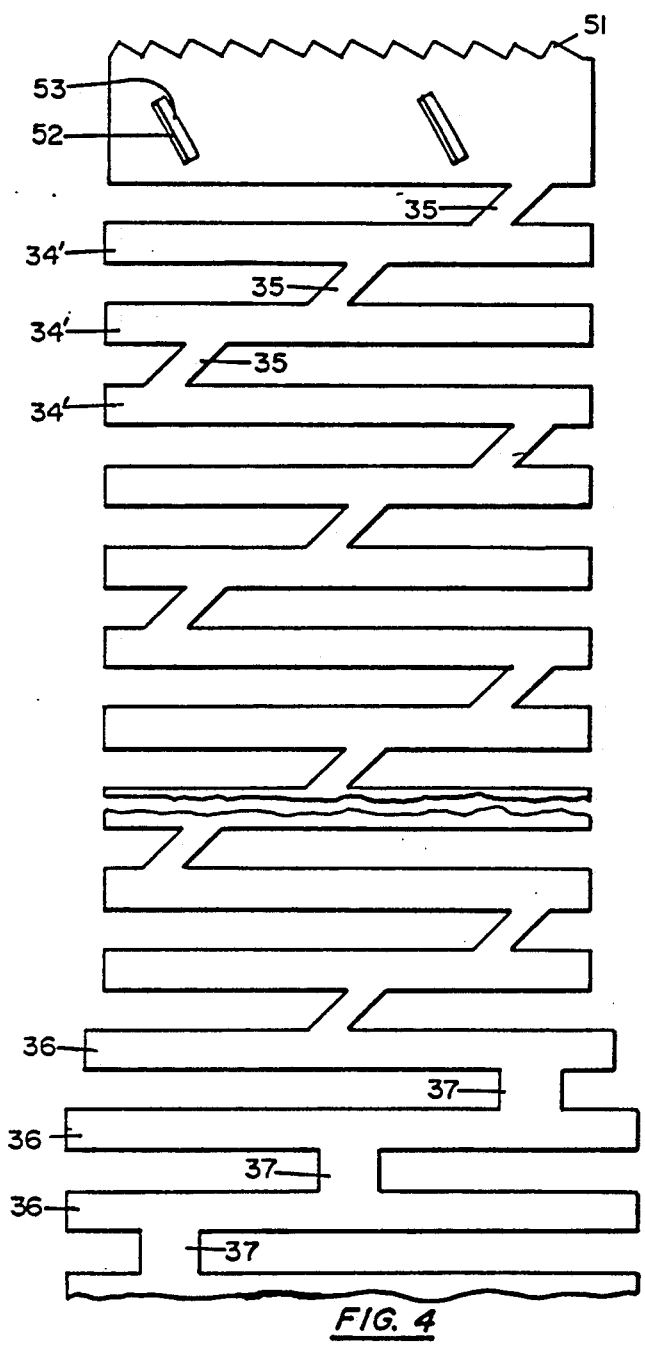
FIG. 4    FIG. 3
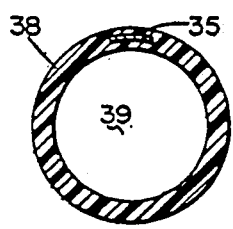
FIG. 7
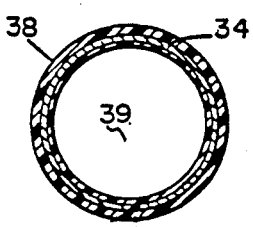
FIG. 6
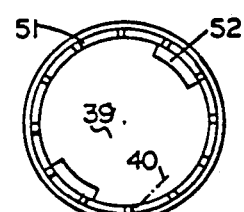
FIG. 5

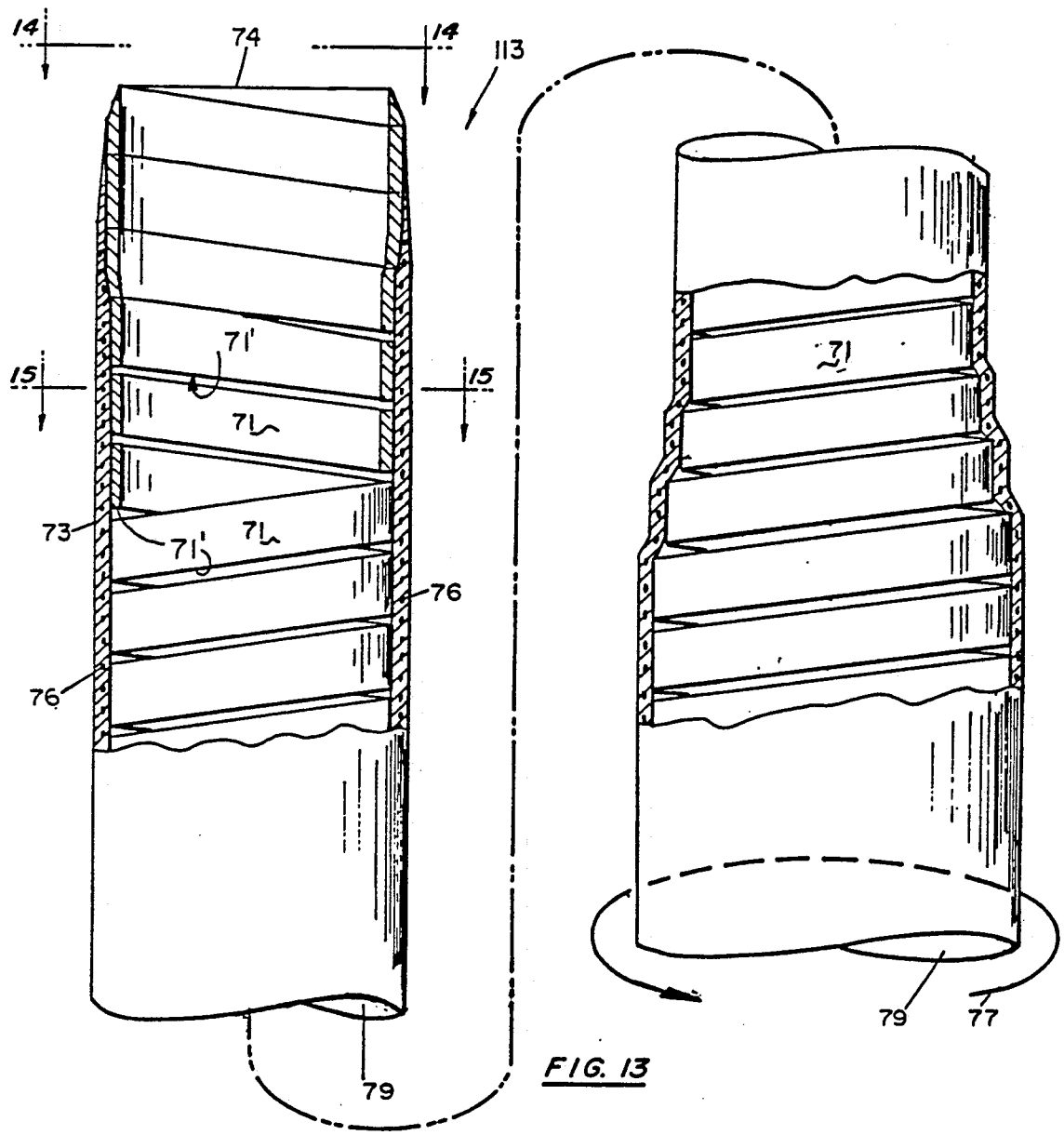
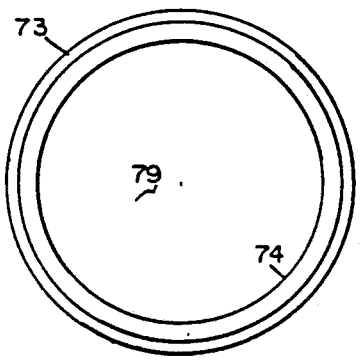
FIG. 14
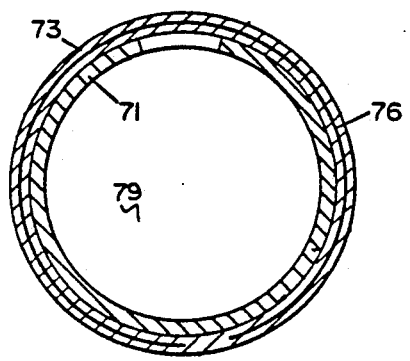
FIG. 15

ROTARY-CATHETER FOR ATHERECTOMY

CROSS REFERENCE TO OTHER APPLICATIONS

This application is a continuation in part (CIP) of application SN 07/286,509 filed Dec. 19, 1988, now U.S. Pat. No. 4,894,051, which is a CIP of these applications, application SN 07/243,900 filed Sept. 13, 1988, now U.S. Pat. No. 4,886,490, which is a CIP of three applications, application SN 07/078,042 filed Jul. 27, 1987, now U.S. Pat. No. 4,819,634, application SN 07/205,479 filed Jun. 13, 1988 now U.S. Pat. No. 4,833,458, and application SN 07/225,880 filed Jul. 29, 1988, now U.S. Pat. No. 4,842,589. These three applications are CIPs of application SN 07/018,083 filed Feb. 24, 1987, which is a CIP of application SN 06/874,546 filed Jun. 16, 1986 (now patent 4,732,154) which is a CIP of application SN 06/609,846 filed May 14, 1984 (abandoned).

All the above applications are being incorporated herein by reference.

BACKGROUND AND OBJECTIVES OF THE INVENTION

With age a large portion of the population develops arterial obstructions formed by fats, fibrous material and calcified deposits, resulting in a diminished blood circulation. These obstructions can induce blood clots which further diminish or block the blood flow. When this occurs in the coronary arteries serving the heart muscles it is referred to as a heart attack. Presently such obstructions are bypassed with a graft or they are treated by angioplasty using a catheter equipped with a balloon which is inserted, over a flexible guide-wire, into the obstruction through the arterial system and then inflated to dilate the obstruction's lumen. Problems with this treatment are that it injures the arterial wall and may burst it. In certain cases it is ineffective. It creates a rough lumen. It does not remove the obstructing material out of the vascular system and may even release obstruction material into the vascular system. Thus, angioplasty during a heart attack carries the risk of dislodging particles of the blood clot and allowing it to move down stream creating further, potentially critical, damage.

An objective of the present invention is to provide a flexible torque transmitting rotary-catheter for an atherectomy system which can be percutaneously or intra-operatively introduced into the vascular system for cutting and removing an obstruction therein. The flexible rotary-catheter is insertable and rotatable over a flexible guide-wire and transmits rotation and torque to rotary coring means at its distal end from a motor affixed to its proximal end.

A further objective of the present invention is to provide a flexible rotary-catheter that would positively remove out of the human body the obstruction material, including blood clots if present, create a smooth lumen, and would minimize injury to the blood vessel's wall.

A further objective of the invention is to provide a system that can be used during a heart attack to provide an immediate relief and a long term correction of the diseased arterial site.

The flexible rotary-catheter should lend itself to be producable in diameters down to around 1mm (millimeter) and a length of around a meter to be able to reach and enter small and remote blood vessels. Preferably, the procedure using the atherectomy system would resemble angioplasty so that present skills of the medical staff can be utilized.

The flexible rotary-catheter should be simultaneously flexible and capable of transmitting torque so that when it is introduced percutaneously to treat an obstruction in a remote artery, for example a coronary artery, it can assume a tortuous path of the vascular system including some sharp turns found in the coronary vascular system.

These and other objectives of the invention will become apparent from the following discussion and the accompanying drawings.

BRIEF DESCRIPTION OF THE FIGURES

FIG. 3 shows a partially sectioned view of a first embodiment of a flexible rotary-catheter.

FIG. 4 shows a skeleton member of the flexible rotary-catheter of the first embodiment in its flat position before it has been rolled to form the intermittent tube shown in FIG. 3.

FIG. 5 shows an end view of the first embodiment viewed along line 5—5 marked on FIG. 3.

FIG. 6 shows a cross sectional view of the first embodiment as viewed along line 6—6 marked on FIG. 3.

FIG. 7 shows a cross sectional view of the first embodiment as viewed along line 7—7 marked on FIG. 3.

FIG. 13 shows a cross sectional view of a fourth embodiment of the flexible rotary-catheter.

FIG. 14 shows an end view of the fourth embodiment as viewed along a line 14—14 marked on FIG. 13.

FIG. 15 shows a cross sectional view of the fourth embodiment as viewed along a line 15—15 marked on FIG. 13.

DETAILED DESCRIPTION OF THE DRAWINGS

Figure 1:
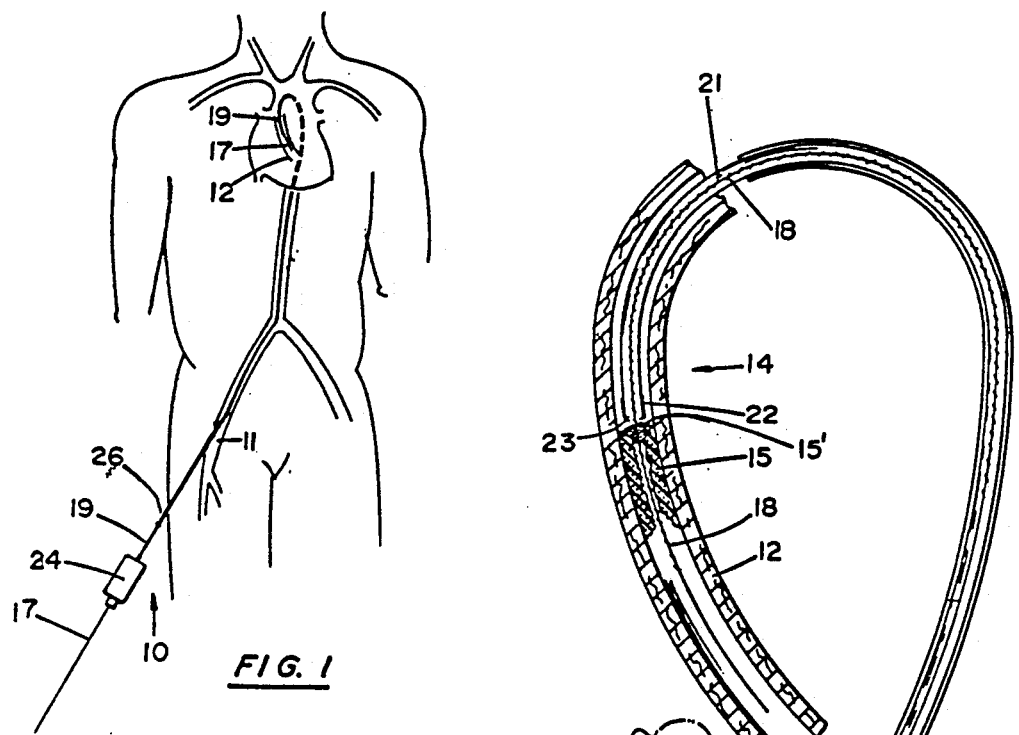
FIG. 1 shows a general view of an atherectomy system being inserted into an obstructed human coronary artery. The atherectomy system is introduced into the vascular system percutaneously at the groin area and is snaked through the arterial system to reach the work site where the obstruction is about to be removed.

FIG. 1 shows a general view of an atherectomy system 10 which is percutaneously introduced into a human femoral artery 11 at the groin area, and its distal end is snaked through the arterial system to reach a work site in a coronary artery 12.

Figure 2:
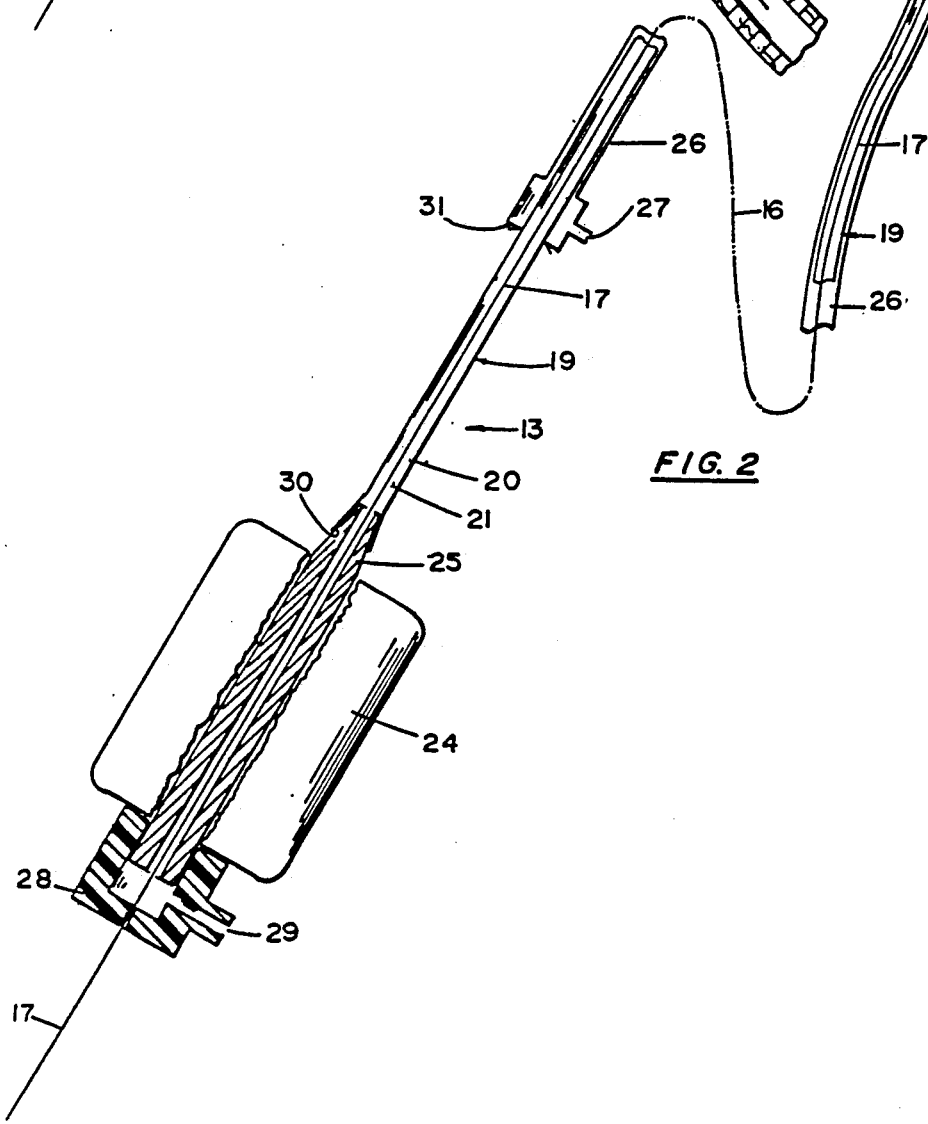
FIG. 2 shows a cross sectional view of the proximal and distal ends of the atherectomy system with its distal end inserted into an obstructed coronary artery. The general positioning of the parts corresponds to their position in FIG. 1. Due to space limitations on the drawing sheets a segment or segments of the atherectomy system and flexible rotary-catheter are omitted and in FIG. 2 the mid section of the system is represented by a phantom line.

FIG. 2 shows an enlarged cross sectional view of a proximal end 13 and of a distal end 14, of the system 10. The distal end is inserted into the diseased coronary artery 12 (as shown in FIG. 2 the atherectomy system comprises several elongated parts in a nested relationship, and their ends shall be referred to as "distal" meaning the end which goes into the vessel and "proximal" meaning the other end, thus, "distal direction" or "distally" shall indicate a general direction from the proximal end to the distal end, and "proximal direction" or "proximally" shall refer to an opposite direction. It should also be noted that the same numbers are used to indicate the same items throughout the FIGURES) containing a blood clot 15' seated on an atherosclerotic obstruction 15. The mid portion of the atherectomy system is represented by a phantom line 16.

The system 10 comprises a flexible guide-wire 17 having a section at its distal end shaped as an auger 18. The flexible guide-wire is designed to be insertable through the human vascular system.

A flexible rotary-catheter 19 has a wall 20 defining a longitudinal channel 21. The catheter 19 is rotatable and slidable over the flexible guide-wire 17. A rotary coring means in the form of a tubular-blade 22 is located at the distal end of the flexible rotary-catheter 19. The tubular-blade 22 defines a through-hole 23 which forms with the channel 21 a continuous passage for accepting the obstruction material ingested into the through-hole (the term rotary coring means as used herein refers to a tubular blade with a smooth or toothed cutting edge, as shown in the drawings accompanying this application or to coring means such as a blade wIth inwardly bent teeth shown in my above incorporated applications SN 06/609,846 and SN 07/225,880 or to a heated tubular blade, an expandable tubular blade or a radiation emitting blade shown in my above incorporated application SN 07/243,900. Some of these rotary coring means are incorporated into, or are part of, the distal end of the flexible rotary-catheter and have no discrete internal wall of their own, in which case the continuous passage consists of the channel 21).

A motor 24 has a hollow tapered shaft 25 which couples it to the proximal end of the flexible rotary-catheter through a matching tapered seat 30 for rotating it around the flexible guide-wire 17.

A sleeve 26 introduces the flexible rotary-catheter into the vascular system and may be extended distally to separate the arterial wall from the rotating catheter and to deliver contrast and/or irrigating fluid to the work site. The sleeve 26 may be formed to a desired shape and serve as a guiding-catheter and assist in guiding the system through the vascular system to the work site. A port 27 is provided to accept fluids for delivery through the sleeve's distal end and a seal 31 prevents the fluids from escaping out of the proximal end of the sleeve.

A rotary joint 28 has a port 29 which is connected through the hollow shaft 25 to the channel 21 and can be used for delivering fluids to the work site or for creating a negative pressure in the channel 21 to assist in drawing the obstruction material proximally. The flexible guide-wire slidably passes through a close fitting hole formed at the proximal end of the rotary joint 28.

FIG. 3 shows a first embodiment of a flexible rotary-catheter 33 having means for diametrical stabilization of the flexible rotary-catheter while transmitting torque and being bent, as for example when cleaning an obstruction located in the coronary arteries illustrated in FIG. 2. The diametrical stabilizing means is in the form of a series of hoop members 34 connected one to the other by the torque transmitting means in the form of strips 35. Collectively the hoops 34 and strips 35 form a skeleton of the flexible rotary-catheter on which a plastic wall 38 is formed to define a channel 39.

FIG. 4 shows a shape cut out of a flat thin material such as stainless steel sheet, including horizontal strips 34' inter-connected by the inclined strips 35. At a later stage the horizontal strips 34' are folded and their ends bonded, or welded, to form the diametrical rigid hoops. As shown on FIG. 5 the ends of the strips 34' can be made to butt and bond along the inclined line 40 to avoid local double thickness of the hoop at the point of connection. The hoops rigidity can be enhanced by giving them a slight arced cross section as shown in FIG. 3. The thin strips 35 bend easily, but only in one direction, therefore they are phased at third of a circle intervals, as shown in FIG. 3 so that everY three consecutive hoops act as a miniature universal-joint that can bend in any direction while transmitting rotation and torque.

During the manufacturing process, while the material is still flat, as shown in FIG. 4, it can be readily accessed with tools and dies, and straight or inwardly bent teeth or paddles 52 can be relatively easily fabricated in it. The paddles can be formed by cutting a rectangular slot 53 along three of its sides and bending the material inwards around the fourth side which is left intact. The paddles 52 assist in pulling the obstruction material proximally in the flexible rotary-catheter 33 by turning the cut obstruction material that enters the through-hole around the stationary auger, and also by being inclined themselves the paddles operate as inclined planes to move the material proximally in the flexible rotary-catheter 33.

The coring action which takes place at the distal end cf the flexible rotary-catheter requires a certain amount of net torque and rotation, however, due to frictional losses along the length of the flexible rotary-catheter the gross torque that is required at its proximal end is substantially larger than the net torque. To withstand the gross torque the shaft may be strengthened by, as shown in FIG. 4, horizontal strips 36 and vertical strips 37 being made longer and wider, respectively, increasing the flexible rotary-catheter diameter (note FIG. 3) and torque transmitting capacity (from hereon the distal small diameter and proximal larger diameter sections of the flexible rotary-catheter will be referred to as the neck and shaft sections, respectively). Since the shaft is often disposed in relatively straight arteries, its increased stiffness is acceptable. To further protect the system and the artery from various unpredictable and uncontrollable variations that may occur during an individual procedure (such as changes in coefficient of friction between the rotating parts of the system and the stationary parts of the system or of the artery, or changes in the forces inducing the friction which may occur due to misalignment of parts of the system, or a spasm in the artery which may lock the artery onto the flexible rotary-catheter and alter the pattern of torque distribution along the flexible rotary-catheter) a torque limiting clutch, as shown in my above incorporated application SN 07/243,900, may be incorporated between the shaft and the neck.

Figure 8:
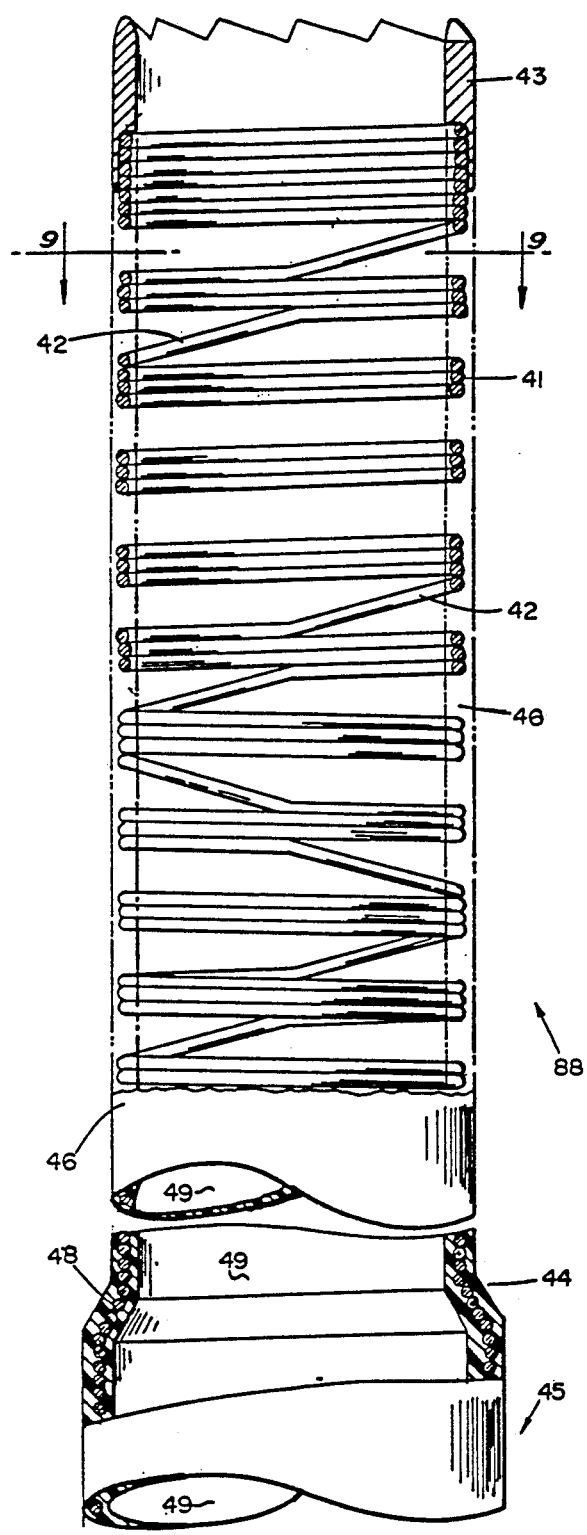
FIG. 8 shows a partially sectioned view of a second embodiment of a flexible rotary-catheter.
Figure 9:
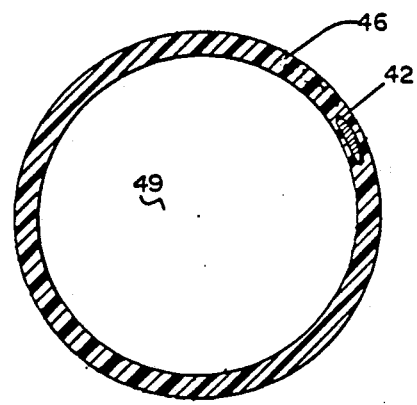
FIG. 9 shows a cross sectional view of the second embodiment as viewed along line 9—9 marked on FIG. 8.
Figure 11:
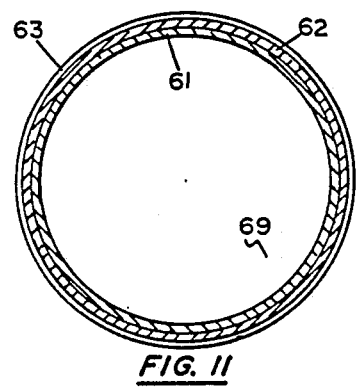
FIG. 11 shows a cross sectional view of the third embodiment as viewed along a line 11—11 marked on FIG. 10.
Figure 12:
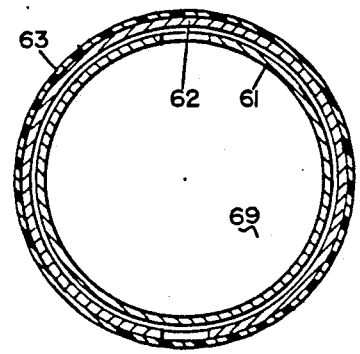
FIG. 12 shows a cross sectional view of the third embodiment as viewed along line 12—12 marked on FIG. 10.

FIG. 8 shows a second embodiment of a flexible rotary-catheter 88 wherein the hoop members are a few closely spaced windings 41 connected one to the other by a widely spaced partial winding 42. The closely spaced windings 41 can be brazed together to increase their diametrical stability. The widely spaced partial windings 42 serve to transmit torque from one hoop to the other and increase the flexibility of the rotary-catheter.

The windings 41, 42 and 48 (which is the continuation of the windings in the shaft section) form a skeleton to which a rotary coring means, in the form of a tubular toothed blade 43, is brazed. The flexible rotary-catheter 88 comprises a neck section which extends from the blade 43 down to a point 44 at which point the rotary-catheter diameter increases to form a shaft section 45 with an increased torque transmitting capacity.

A plastic wall 46 is formed to complete the flexible rotary-catheter's structure and define a channel 49 therein. The fact that the skeleton of the second embodiment is made of a continuous wire simplifies the handling and fabrication of the flexible rotary-catheter, however, notwithstanding this, individual hoop members can be used to stabilize the flexible rotary-catheter's diameter in which case the plastic wall itself transmits the torque.

Figure 10:
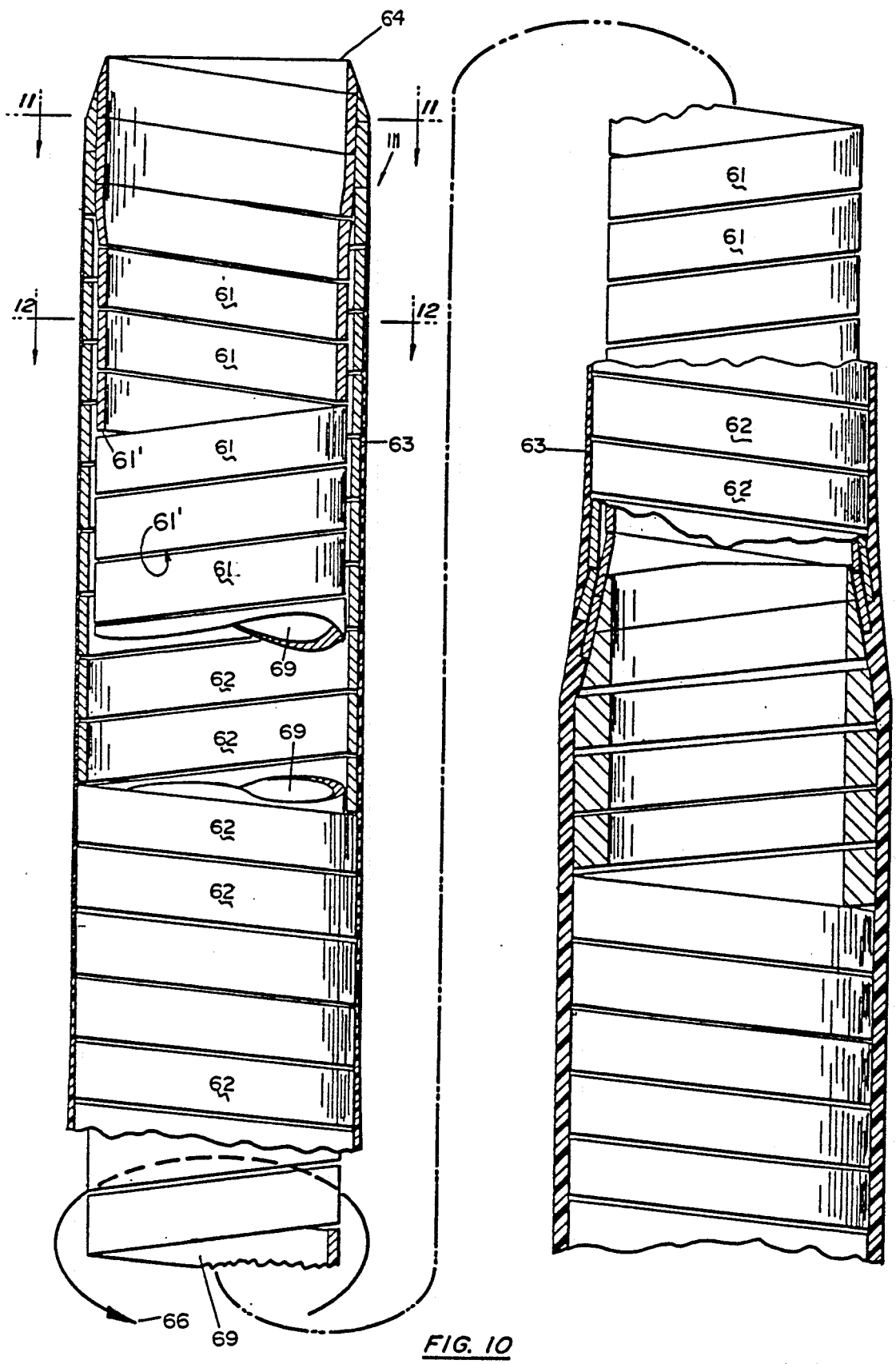
FIG. 10 shows a sectioned view of a third embodiment of the rotary-catheter.

FIG. 10 shows a third embodiment 111 of a flexible rotary-catheter wherein the means for diametrical stabilization and for transmitting torque comprise an inner helix 61 wound in the direction of rotation (which means that moving along the coils of the inner helix in the direction of rotation illustrated by arrow 66 on FIG. 10, while the helix is stationary, would cause advancing from the proximal end to the distal end). It can be visualized that when the inner helix is rotated in the direction of arrow 66, the proximal edge 61' of the ribbon which, due to the spacing between the coils contacts the obstruction material, will act on the material in the continuous passage as an inclined plane means and assist the obstruction material in moving proximally. Modifying the spacing or slightly bending the ribbon so as to increase its proximal edge's protrusion into the continuous passage will increase the effectiveness of such inclined plane means. The winding of the inner helix would tend to diametrically expand when the motor 24 drives the flexible rotary-catheter 111 in the direction of the arrow 66, however, a second outer helix 62 wound in the counter-rotation direction tends to contract and thereby restrain the expansion of the first helix 61 and assist it in transmitting torque.

It is desirable to minimize the catheter's wall thickness to allow easy ingestion of cored obstruction material. The ribbon forming the outer helix is under longitudinal and radial tension whereas the ribbon forming the inner helix is under longitudinal and radial compression. As the catheter transmits torque the inner coil is subjected to bending and buckling as well as compressive loads requiring the usage of a thicker ribbon for the inner coil than what is needed for the outer coil, this will optimize strength and flexibility while minimizing the wall thickness of the catheter.

A plastic wall 63 seals a channel 69 defined by the rotary-catheter 111 so that negative pressure or fluid introduced at its proximal end would reach its distal end. Alternatively, a thin plastic layer can be inlaid between the helixes to minimize friction between them.

When the helixes are made of flat ribbon material as shown in FIG. 10 they form a wall which does not seal fluids effectively but may be sufficient for the purposes of mechanically containing the cut obstruction particles without the plastic layer 63. Therefore, if fluid conveyance or suction through the flexible rotary-catheter are not needed, the plastic wall 63 may be omitted to increase flexibility and decrease wall thickness of the flexible rotary-catheter, and a thin slippery coating may be applied to the ribbons which are used to form the helixes, to minimize friction between the helixes and of the helixes with their surroundings.

A rotary coring means in the form of tubular blade 64 is made as an integral part of helixes 61 and 62, the last few coils of which are brazed together at their distal end and then sharpened.

FIG. 13 shows a partially sectioned view of the fourth embodiment 113 of the flexible rotary-catheter wherein the means for diametricaly stabilizing and for transmitting torque comprise a helix 71 wound in the direction of rotation (such windings would tend to diametrically expand when the motor drives the flexible rotary-catheter 113 in the direction of the arrow 77), and an external restraining member in the form of a wall 73 which restrains such expansion (the wall's cross-sectional marking is standard single line marking so as to not obscure a cord 76 which is integrated therein). The wall restraining action is reinforced by diametrical restraining means 76 in the form of cord made of, for example, nylon or aramid fibers which restrain the diametrical expansion of the helix 71 but have little effect on the wall's ability to stretch along its longitudinal axis and therefore on its ability to bend as shown in FIGS. 1 and 2. The wall 73 defines a fluid worthy channel 79. A proximal edge 71' of the ribbon which, due to the spacing between the coils contacts the obstruction material, will act on the material in the continuous passage as an inclined plane means and assist the obstruction material in moving proximally. Modifying the spacing or slightly bending the ribbon so as to increase its proximal edge's protrusion into the continuous passage will increase the effectiveness of such inclined plane means.

A rotary coring means in the form of a tubular blade 74 is made as an integral part of the helix 71, the last few coils of which are brazed together at their distal end and then sharpened, as shown in FIG. 10.

The present invention puts in the hand of the physician a method to immediately and effectively intervene in what is often referred to as a "heart attack" which is commonly caused by an obstruction made of a soft fresh blood clot formed on an atherosclerotic plaque which has developed for several years. Currently, the presence of the fresh blood clot, which has jelly like consistency, deters angioplasty since angioplasty may dislodge and release downstream some of the blood clot's material causing additional arterial occlusions possibly at points which would be more difficult to treat or points where no alternate blood supply exists (at the point of the original obstruction, being an "old" obstruction, alternate blood supply may have developed). Currently, several pharmacologic treatments are being tested that dissolve the blood clot, after which angioplasty may be performed, however, because the present invention is effective in releasing and removing blood clots as well as atherosclerotic plaque it circumvents the delay and added risks that the pharmacologic treatment introduces, such as for example bleeding elsewhere.

The process for removing an obstruction made of a soft blood clot 15' formed on an atherosclerotic plaque from a blood vessel 12, comprises the following steps:

inserting into the blood vessel a flexible guide-wire 17 and advancing it into the blood clot 15' which formed on the obstruction 15, inserting into the blood vessel, over the flexible guide-wire, the flexible rotary-catheter 19 having a proximal end 13 and a distal end 14 with a rotary coring means affixed thereto, advancing the distal end 14 to mechanically engage and unseat the blood clot 15' while applying suction to port 29 to suck the blood clot 15' into the through-hole 23, advancing the rotary coring means to rotatably engage and cut the atherosclerotic plaque of the obstruction 15, removing the system with the blood clot and the atherosclerotic plaque out of the blood vessel 12.

While the present invention has been illustrated by a limited number of embodiments, it should be understood that various modifications and substitutions may be made without departing from the spirit of the invention or the scope of the claims.

I claim:

1. An atherectomy system insertable into a human blood vessel for coring and removing an obstruction therein, comprising in combination:
   a flexible guide-wire insertable into said blood vessel,
   a flexible rotary-catheter defining continuous passage and being rotatably disposed and slidable over said flexible guide-wire, said flexible rotary-catheter having a proximal and distal ends,
   a rotary coring means for cutting and ingesting obstruction material, located at said distal end,
   a coupling means for rotating said flexible rotary-catheter around said flexible guide-wire, located at said proximal end,
   means for diametricaly stabilizing and means for transmitting torque being incorporated in said flexible rotary-catheter.

2. An atherectomy system as in claim 1, wherein said flexible rotary-catheter is rotatably disposed in a sleeve.

3. An atherectomy system as in claim 1, wherein said means for diametricaly stabilizing said flexible rotary-catheter comprise a series of hoop members connected one to the other by said torque transmitting means.

4. An atherectomy system as in claim 3, wherein said hoop members are rolled strips connected one to the other by strips.

5. An atherectomy system as in claim 3, wherein said hoop members are closely spaced windings connected one to the other by a widely spaced winding.

6. An atherectomy system as in claim 1, wherein said means for diametricaly stabilizing the flexible rotary-catheter comprise a helix.

7. An atherectomy system as in claim 6, wherein said helix is wound in the direction of rotation and having a member restraining the exPansion of said helix, said helix carrying at least part of the torque transmitted through said flexible rotary-catheter.

8. An atherectomy system as in claim 7, wherein said external restraining member comprise a helix wound in the counter rotation direction.

9. An atherectomy system as in claim 6, having a plastic wall defining a fluid worthy channel through said flexible rotary-catheter.

10. An atherectomy system as in claIm 9, wherein said plastic wall contains diametrical restraining means.

11. An atherectomy system as in claim 1, wherein said rotary coring means is an integral part of said means for diametricaly stabilizing said flexible rotary-catheter.

12. An atherectomy system as in claim 1, wherein said rotary coring means is an integral part of said means for transmitting torque.

13. An atherectomy system insertable into a human blood vessel for coring and removing an obstruction therein, comprising in combination:
    a flexible guide-wire insertable into said blood vessel,
    a flexible rotary-catheter defining continuous passage and being rotatably disposed and slidable over said flexible guide-wire, said flexible rotary-catheter having a proximal and distal ends,
    a rotary coring means for cutting and ingesting obstruction material, located at said distal end,
    a coupling means for rotating said flexible rotary-catheter around said flexible guide-wire, located at said proximal end,
    inclined plane means being located in said continuous passage for assisting the obstruction material in moving proximally therein.

14. An atherectomy system as in claim 13, wherein said flexible rotary-catheter is rotatably disposed in a sleeve.

15. An atherectomy system as in claim 14, wherein said flexible rotary-catheter comprise a helix.

16. An atherectomy system as in claim 15, wherein said helix is wound in the direction of rotation.

17. An atherectomy system as in claim 16, wherein a diametrical restraining member restrains said helix.

18. An atherectomy system as in claim 17, wherein said restraining member comprise an external helix wound in the counter rotation direction.

19. An atherectomy system as in claim 17, wherein said restraining member comprise a plastic wall.

20. An atherectomy system as in claim 19, wherein said wall contains diametrical restraining means.

21. A process for removing from a human blood vessel an obstruction made of a soft blood clot formed on an atherosclerotic plaque, comprising the following steps:
    inserting into the blood vessel a flexible guide-wire and advancing it into the obstruction,
    inserting into the blood vessel, over the flexible guide-wire, a flexible rotary-catheter having a proximal end and a distal end with a rotary coring means at the distal end,
    advancing the distal end to mechanically engage and unseat the blood clot while applying suction to the proximal end to ingest the blood clot into the distal end,
    rotating and advancing the rotary coring means to cut and swallow the atherosclerotic plaque,
    removing the system with the blood clot and the atherosclerotic plaque from the blood vessel.

22. A process as in claim 21, wherein, at least a portion of the flexible guide-wire is shaped as an auger.

* * * * *